United States Patent
Suzuki et al.

(10) Patent No.: US 7,694,644 B2
(45) Date of Patent: Apr. 13, 2010

(54) METHOD AND DEVICE FOR PATTERN COATING

(75) Inventors: Migaku Suzuki, Tokyo (JP); Toa Kobayashi, Tokyo (JP); Reiko Moriya, Tokyo (JP); Satoru Wakabayashi, Nara (JP); Satoshi Ukawa, Nara (JP)

(73) Assignee: DSG International Limited, Tortola (VG)

( * ) Notice: Subject to any disclaimer, the term of this patent is extended or adjusted under 35 U.S.C. 154(b) by 1305 days.

(21) Appl. No.: 10/542,080

(22) PCT Filed: Jan. 16, 2003

(86) PCT No.: PCT/JP03/00308

§ 371 (c)(1),
(2), (4) Date: Jul. 13, 2005

(87) PCT Pub. No.: WO2004/062816

PCT Pub. Date: Jul. 29, 2004

(65) Prior Publication Data

US 2006/0153984 A1 Jul. 13, 2006

(51) Int. Cl.
  *B05C 1/00* (2006.01)
(52) U.S. Cl. .................. 118/102; 118/106
(58) Field of Classification Search ............. 118/106, 118/102, 103, 112, 118, 206, 257, 44; 425/89, 425/373; 162/361, 362, 110; 427/356, 271, 427/277, 278, 299, 358, 359, 361
See application file for complete search history.

(56) References Cited

U.S. PATENT DOCUMENTS

| | | | | |
|---|---|---|---|---|
| 4,097,210 A | * | 6/1978 | Romanillos | 425/89 |
| 4,222,722 A | * | 9/1980 | Bokelmann | 425/89 |
| 6,183,847 B1 | | 2/2001 | Goldwasser | |
| 6,420,100 B1 | | 7/2002 | Trokhan et al. | |

FOREIGN PATENT DOCUMENTS

| | | |
|---|---|---|
| EP | CH 669 915 A5 | 4/1989 |
| JP | 61-293575 A | 12/1986 |
| JP | 08-309256 A | 11/1996 |
| JP | 10-168230 A | 6/1998 |
| JP | 2000-005674 A | 1/2000 |
| JP | 2001-258937 A | 9/2001 |
| JP | 2001-1271262 | 10/2001 |

OTHER PUBLICATIONS

Supplementary European Search Report; Oct. 24, 2006.

* cited by examiner

*Primary Examiner*—Brenda A Lamb
(74) *Attorney, Agent, or Firm*—Frommer Lawrence & Haug LLP; Ronald R. Santucci

(57) ABSTRACT

A method for coating a dispersion slurry containing a solid SAP dispersed in a dispersion medium on a surface of a substrate sheet are provided. The method is characterized in that a first region and a second region are formed on the surface of the substrate sheet with a convex-and-concave pattern wherein the first region have the coating layer in thicker thickness and the second region have the coating layer in thinner thickness or does not scarcely have the coating layer, by means of positioning the rotating pattern roll over the substrate sheet via the cover film, of supplying the dispersion slurry between the substrate sheet and the cover film while rotating the rotating pattern roll, and of pushing the coating layer with the rotating pattern roll via the cover film, when the coating layer of the dispersion slurry is formed.

11 Claims, 9 Drawing Sheets

P>Q
Q=2〜300mm
SAP;P:100〜500g/m²
SAP;Q:10〜150g/m²

METHOD AND DEVICE FOR PATTERN COATING

This application is a 371 of PCT/JP2003/000308 filed on Jan. 16, 2003 and published on Jul. 29, 2004 under publication number WO 2004/062816 A1.

FIELD OF INVENTION

The present invention relates to a method of and an apparatus for coating, to manufacture a highly-water-absorbing sheet which incorporates a layer of highly-water-absorbing coating containing water-absorbing solids such as a super-absorbent polymer (hereinafter referred to as "SAP") on the surface of a substrate sheet such as a non-woven fabric; especially it relate's to a method and improved apparatus for pattern-coating to obtain a highly-water-absorbing sheet with superior physical properties such as liquid diffusivity and flexibility.

BACKGROUND ART

In case of executing a coating process on a surface of various substrate sheets, dispersion slurry with solid particulates dispersed in dispersion medium, a partial change in concentration of each components occurs due to phase separation, precipitation, and aggregation, unlike in the case that a liquid to be coated is a uniform solution. When a dispersion slurry is coated, of various coating apparatuses, it is preferred that a roll-coating apparatus, which is relatively simple in structure and low in equipment cost, is used. However, a conventional method of roll-coating is prone to cause precipitation of solid particulates in the dispersion slurry or their adhesion to the surface of the coating roll. As a result, uneven coating surface and clogging during a job run among other things, occur, making a uniform and stable coating process difficult.

In order to alleviate adhesion of dispersion slurry to the roll surface as described above, ingenious approaches, including providing a surface finish on the surface of the coating roll with strippable material such as silicone and Teflon™, scraping off by incorporating a scraper, creating a strippable condition by rotating the roll in a forward or a backward direction, etc., have been performed.

The conventional countermeasures, however, have not fully solved the above problems that the dispersion slurry adheres to the coating roll surface. Such the adhesion is a common phenomenon in contact-type coaters, including not only roll-coaters but also bar-coaters and knife-edge-coaters where a coater directly contacts with a substrate. In order to fundamentally prevent such troubles, in the conventional level of technology, there is no alternative-but to employ a non-contact-type coater, such as a curtain-coater, grid-coater, or spray-coater, in place of a contact-type coater. This, however, will newly add limiting factors to the properties of dispersion slurry for coating and complicate the apparatus for coating, and greatly increase the equipment cost as well. Especially, in the case of the dispersion slurry, with water-absorbing solid particulates called "SAP" dispersed in the water-organic-solvent-mixture dispersion medium, such as the subject of the present invention, because of the strong surface tack of the water-absorbing solid particulates, significant troubles tend to occur in the conventional non-contacting type of coating apparatus, making it extremely difficult to execute a uniform and stable coating process.

On the other hand, the obtained super-absorbent sheet will not be able to offer satisfactory properties in the case that the sheet is applied for diapers, feminine protection products and other sanitary products, even if a super-absorbent coating layer is formed on the substrate sheet by overcoming the aforementioned difficulties. One of the reasons is that if a super-absorbent coating layer is provided so as to entirely cover one of the surfaces of the substrate sheet, even if the substrate sheet is as soft and highly flexible as non-woven fabric, the flexibility required of the water-absorbing sheet is lessened due to stiffness of the super-absorbent coating layer and thus it cannot meet the performance criteria sought for the above sanitary products. Furthermore, a super-absorbent sheet comprising a super-absorbent coating layer entirely covering one of the surfaces of the substrate sheet may have an adequate water absorbing capacity, and an absorbing speed of the sheet depends on that of the coating layer. As a result, when the liquid exceeding the absorbing speed in volume is supplied, the liquid which has failed to absorb in the absorbing layer/the sheet will remain there, thus becoming the cause of leakage.

The inventors of the present invention have proposed that in order to correct these shortcomings, a technique of coating the surface of the substrate sheet while leaving a part of it uncoated (as in for example, Japan Patent Laid-open 10-168230A and Japan Patent Laid-open 2000-005674A). In this technique heretofore known, a water-absorbing layer in multiple band shape extending along the longitudinal direction of the substrate sheet is formed by supplying the slurry in multiple band shape on the surface of the moving substrate sheet. The region where water-absorbing coating layer is present and the region where it is not present, or in other words the region where the substrate sheet is exposed, are mixed on the surface of this super-absorbent sheet. As the result, the liquid which has failed to be absorbed in the water-absorbing coating layer will be diffused in the region where the water-absorbing coating layer is not present, to other areas by the substrate sheet's diffusivity, thereby shortening the time of the liquid's retention and, as a result, alleviating the problem of leakage.

The water-absorbing coating layer is continuous in the longitudinal direction, though it is discontinuous in the width direction of the substrate sheet. Therefore, diffusivity and flexibility are obtained in the width direction, but not in the longitudinal direction, making it impossible to obtain satisfactory performance.

Such defects in the longitudinal direction can be solved by intermittently supplying the dispersion slurry, when coating, to make the coating layer in the longitudinal direction discontinuous. Furthermore, a discontinuous coating layer both in width and longitudinal directions can be achieved by combining it with a technique to make it discontinuous in the width direction, as described above.

SUMMARY OF THE INVENTION

An object of the present invention is to provide a highly-water-absorbing sheet which has sufficient flexibility in both the longitudinal and width directions, as well as superior liquid diffusivity, by means of forming the coating layer of discontinuous pattern in the longitudinal direction, and further of forming the coating layer of discontinuous pattern in both the longitudinal and width directions on the surface of the substrate sheet.

According to the present invention, the present invention provides:

A method for pattern-coating a dispersion slurry containing a water-absorbing solid dispersed in a liquid medium on a surface of a substrate sheet, comprising the steps of:

forming a layer containing said dispersion slurry between a upper layer and a lower layer by supplying the dispersion slurry in a space between an upper layer and an lower layer, said upper layer being a flexible cover film and said lower layer being the substrate sheet traveling under said upper layer, and filling said space with said dispersion slurry; and forming a convex-and-concave pattern on said layer containing dispersion slurry by rotating a rotating pattern roll having a convex-and-concave pattern at the circumference surface thereof into the same direction as the traveling direction of the substrate sheet, while pushing said flexible cover film with the convex portions from upper portion of said flexible cover film.

Further, according to the present invention, the present invention provides:

A method for pattern-coating a dispersion slurry containing a water-absorbing solid dispersed in a dispersion medium on a surface of a substrate sheet, comprising the steps of:

forming a coating layer containing said dispersion slurry on the surface of said substrate sheet, by positioning a rotating pattern roll having a convex-and-concave portion at the circumference surface thereof above said substrate sheet traveling into the longitudinal direction of the sheet via a cover film, and by continuously supplying said dispersion slurry between said substrate sheet and said cover film while rotating said rotating pattern roll in the same direction as the traveling direction of said substrate sheet; and forming a first region and a second region on the surface of said substrate sheet, said first region having said coating layer in thicker thickness and said second region having said coating layer in thinner thickness or scarcely not having said coating layer, with a pattern corresponding to the pattern of said convex-and-concave portion, by pushing said coating layer with said rotating pattern roll via said cover film.

In the present invention, the preferred flexible cover film has a contraction and expansion elasticity with 50% or greater of rupture elongation, or a non-elastic film with 50% or less of rupture elongation.

The flexible cover film may be composed of a film with a contraction and expansion elasticity and a non-elastic film, and it may also be a film wherein a film with contraction and expansion elasticity is partially overlapped with a non-elastic film.

If the water-absorbing solid is SAP, the amount of SAP contained in a coating layer is, when converted to the basis weight of SAP, preferably 50 to 500 g/m$^2$ in the first region, 10 to 150 g/m$^2$ in the second region, more preferably in the range of less than 10 g/m$^2$.

The SAP in the solid form preferably has 1500 μm or less in its particulate diameter of its spherical approximation in the particulates, powders or flaky form. A mixed solvent of organic solvent and water is suitable as the dispersion medium, the organic solvent having a swelling-inhibition effect with respect to the SAP. Further, the substrate sheet is preferably a liquid-pervious non-woven fabric.

The dispersion medium is a hydrated-organic medium with water content of 20% or more which partially has a swelling effect with respect to the SAP, while in the dispersion medium the SAP is in a swelled state of twice its self-weight or more, and ten times its self-weight or less, and the substrate sheet is a non-woven fabric.

A dispersion slurry containing a three-component system may be used as the dispersion slurry, wherein a highly defibrillated fiber of wood pulp is added to the dispersion slurry containing a three-component system as an additives, i.e. the third component of the three-component system, in addition to the dispersion medium and the SAP. In this case, it is desirable that the highly defibrillated wood pulp as the additive, is 1 mm or less of fiber length, 250% or less of water retention value, and its loadings are to be 2 to 10% of the SAP.

Further, the present invention provides an apparatus for coating the surface of a substrate sheet with dispersion slurry, the dispersion slurry containing a water-absorbing solid particle dispersed in a dispersion medium. The apparatus is that:

An apparatus for pattern-coating a dispersion slurry containing a water-absorbing solid dispersed in a dispersion medium on a substrate sheet, comprising:

a traveling mechanism for traveling said substrate sheet into the longitudinal direction thereof a rotating pattern roll having a predetermined convex-and-concave pattern on the circumference surface thereof such that the center of axle is vertically positioned;

a cover film for covering the circumference surface of said rotating pattern roll to prevent said dispersion slurry from being contact with the circumference surface of said rotating pattern roll, a front end of said cover film being positioned in the downstream from the lowest position of said rotating pattern roll; and a slurry supplier for continuously supplying said dispersion slurry on the said substrate sheet from a discharge portion of said supply supplier at a outlet position being positioned between said cover film and said substrate sheet;

wherein said apparatus is constituted such that a first region and a second region are formed on the surface of said substrate sheet, the first region having said coating layer in thicker thickness and the second region having said coating layer in thinner thickness or scarcely not having said coating layer, with a pattern corresponding to the pattern of said convex-and-concave portion of said rotating pattern roll, by pushing said coating layer with said rotating pattern roll via said cover film.

It is preferred that the end of the cover film is not fixed.

Also, the diameter of the rotating pattern roll may be, for example, in a range between 100 and 500 mm. The end of the cover film may be extended in the traveling direction of the substrate sheet by 1 to 50 mm to the downstream side from the lowest end of the rotating pattern roll.

Furthermore, both ends of the cover film, excluding its end portion in the traveling direction of the substrate sheet, may be fixed by side seal portions on both ends in the axial direction of a coating roll.

It is suitable that the length between the adjacent convex portions of convex-and-concave pattern formed in the surface of the rotating pattern roll in the rotating direction is, for example, a distance between 2 and 20 mm, the distance being shorter than a distance between rear end of the convex portion and front end of the adjacent convex portion, in view of the traveling direction of the rotating pattern roll.

In addition, in another embodiment of the present invention, the pattern-coating apparatus includes a line-coating plate to supply dispersion slurry on the surface of the substrate sheet in the multiple band shape.

Further, a support roll facing opposite a rotating pattern roll, with a substrate sheet in between, maybe installed at the location where the circumferential surface of a rotating pattern roll comes closest to the surface of the substrate sheet.

Furthermore, seal plates may be installed at the location where the dispersion slurry is supplied to the surface of the substrate sheet, to prevent the substrate sheet from permeating a part of the dispersion slurry and letting it flow down to the lower side of the substrate sheet.

A mechanism to let a substrate sheet travel is, for example, a conveyor to transfer the substrate sheet.

The apparatus is further characterized in that:

The apparatus for coating includes said slurry supplier which is a temporary retaining portion for said dispersion slurry, and said apparatus is further constituted such that:

said substrate sheet is positioned just on said traveling mechanism;

said cover film is positioned on said substrate sheet;

said rotating pattern roll is positioned above said cover film;

said discharge portion of said supply supplier of said temporary retaining portion is the lowest portion of said rotating pattern roll in the upstream direction.

DESCRIPTION OF PREFERRED EMBODIMENT

The "water-absorbing solid" used in the present invention retains, in general, an amount of water absorption under no load at least ten times its self-weight or more. The absorbing solid refers, for example, a solid body, called SAP (superabsorbent polymer), such as a polyacrylilates, a cellulose derivatives, and a polyamino acids; water-absorbing solids of a natural polysaccharide such as grafted starch, and the polysaccharide of a glucomannans (amorphophalus konjak power), or inorganic water-absorbing solids such as silica gel and zeolite. Because these water-absorbing solids swell or gelate in a water-retaining state and become difficult to handle, a method for preparing a slurry containing the water-absorbing solids dispersed in water-containing solvent medium, as a dispersion medium, is used, the water-containing medium being, for example, organic solvent, which have a swelling inhibitive effect against water, such as ethanol, methanol or isopropyl alcohol, the water-containing solvent medium containing 20% or more of water, preferably 30 to 60% of water. Especially, in the case of SAP used as water-absorbing solid, using the ion-exchanged water, the water-absorbing solid retain at least one hundred times or more of an amount of water absorption with respect to its self-weight, and in case of SAP having high water-absorbing capacity, one thousand times of an amount of water absorption with respect to its self-weight. The SAP used as water-absorbing solid is in 2 times to 10 times of water-swelling state with the above-mentioned water-containing solvent medium. Therefore, the dispersed solids is easily bounded or aggregated with each other. In the conventional techniques, the water-absorbing solid as three-component slurry is stabilized by adding microfibrillated cellulose, such as highly defibrillated pulp (preferably of 1 mm in number average fiber length or shorter, when measured by the Kajaani method, and 250% or less water retentivity by Tappi method). However, an attempt to stabilize the dispersion slurry does not fully solve the problems. The conventional method, such as the one described in Japan Patent Laid-open No. 2001-271262 and Japan Patent Laid-open No. 2001-258937, for example, of discharging the coating material by using the head difference does not easily achieve stable coating, either, so it is necessary to incorporate the method of forcibly extruding the coating material, as proposed in the present invention.

Figure 1:
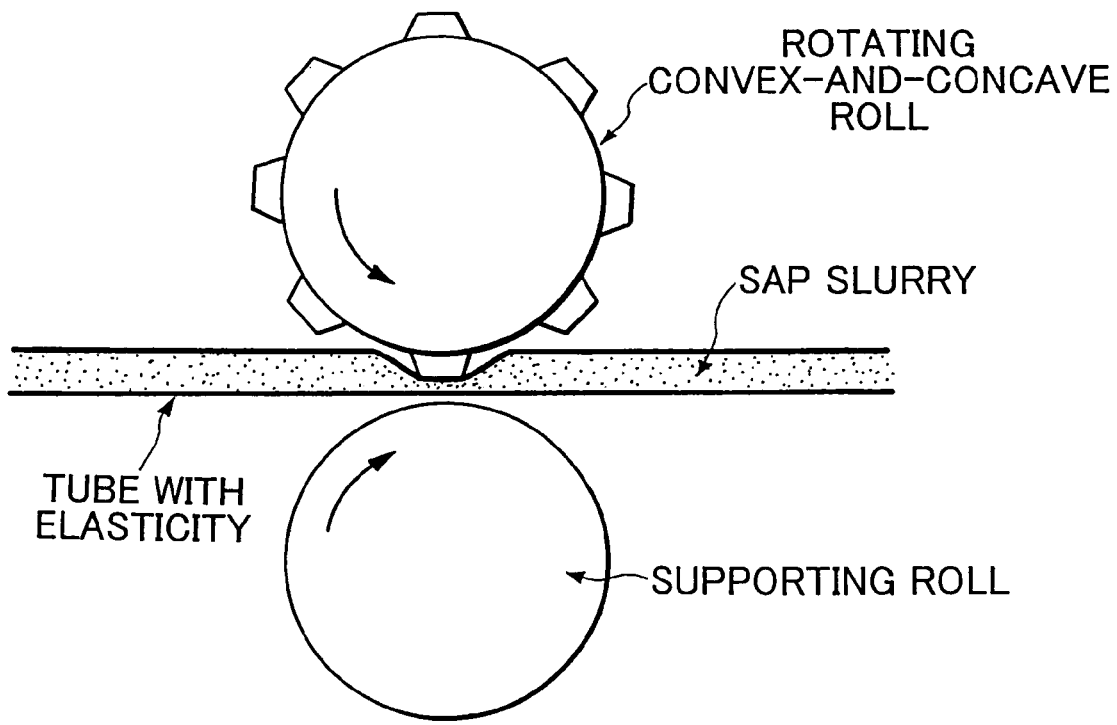
FIG. 1 is an explanatory drawing showing the principle of the tube pump, to explain the principle of coating action according to the coating method of the present invention.

Hereinafter, the principle of the present invention will be explained in reference with FIGS. 1 and 2. FIG. 1 shows the principle of the tube pump. A SAP slurry is put in and passes through the tube with elasticity (hereinafter referred to as the elastic tube), and the SAP slurry is extruded by rotating a flat roll and a rotating convex-and-concave-pattern roll in combination, resulting in a kind of peristaltic motion effect.

Figure 2:
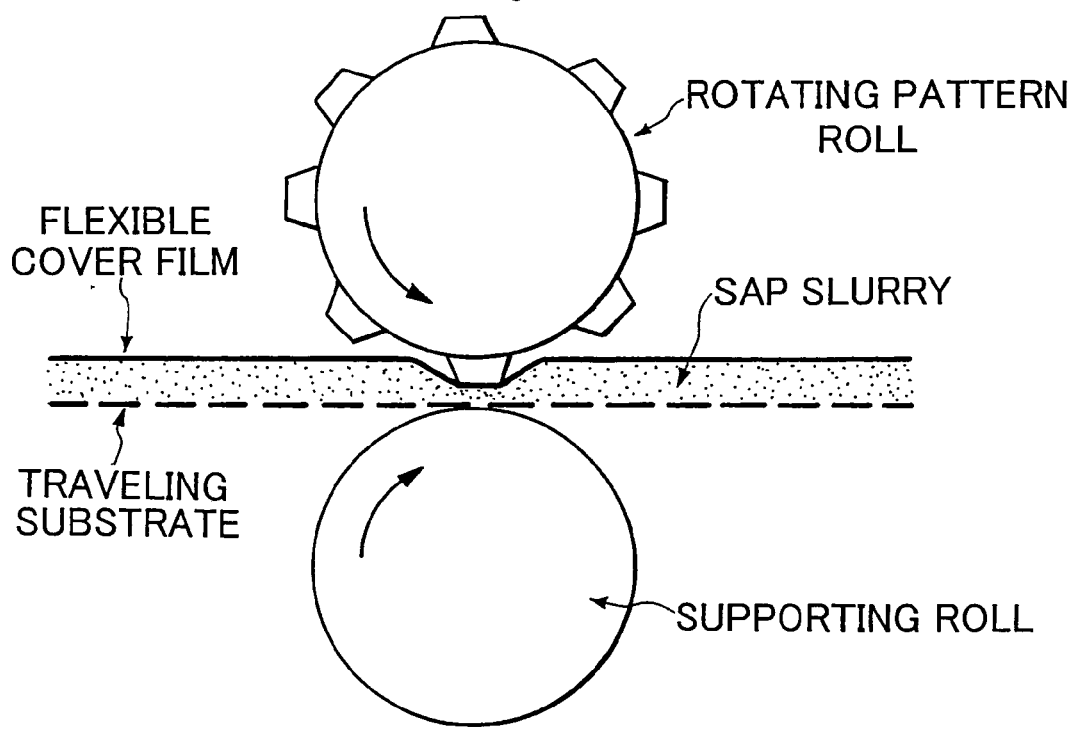
FIG. 2 is an explanatory drawing showing the process of forming the concave-and-convex pattern on the slurry layer according to the principle of the tube pump.

FIG. 2 is a drawing of the principle of the present invention. Instead of an elastic tube of the tube pump as shown in FIG. 1, a SAP slurry is put in and passes through the space between a traveling substrate sheet and a flexible cover film (sealed at both sides), and the SAP slurry is extruded while a pattern roll with convex-and-concave surface is being rotated.

Hereinafter, the fundamental configuration of the apparatus according to the present invention will be explained in reference with Figures.

Figure 3:
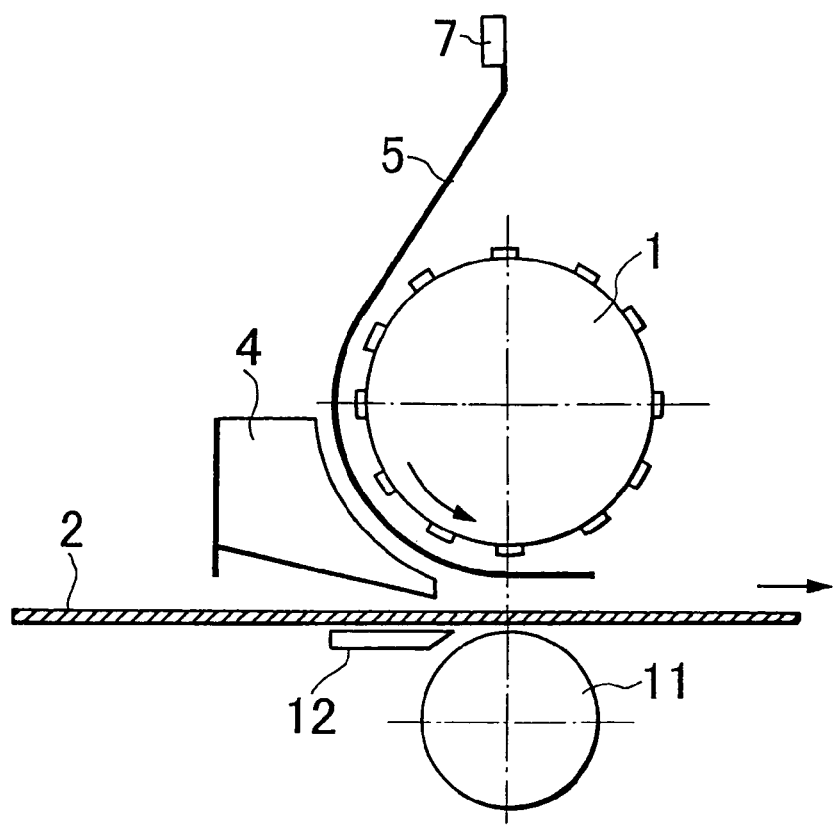
FIG. 3 is a schematic side view of the pattern coating apparatus according to an aspect of the present invention.

FIG. 3 shows an aspect of the coating apparatus according to the present invention. The coating apparatus comprises a rotating pattern roll 1, wherein the rotating pattern roll is positioned such that the center of axle of the rotating pattern roll is substantially horizontal and the rotating pattern roll rotates around the center of axle at the desired rotating speed. In the coating apparatus, a substrate sheet 2 is positioned under the rotating pattern roll 1 such that the substrate sheet 2 continuously travels through a portion close to the lowest end of the moving range of the circumference surface of the rotating pattern roll, by a traveling mechanism which is not illustrated in the figure, during the rotating process to the tangential direction with respect to the circumference surface of the rotating pattern roll 1.

Figure 4:
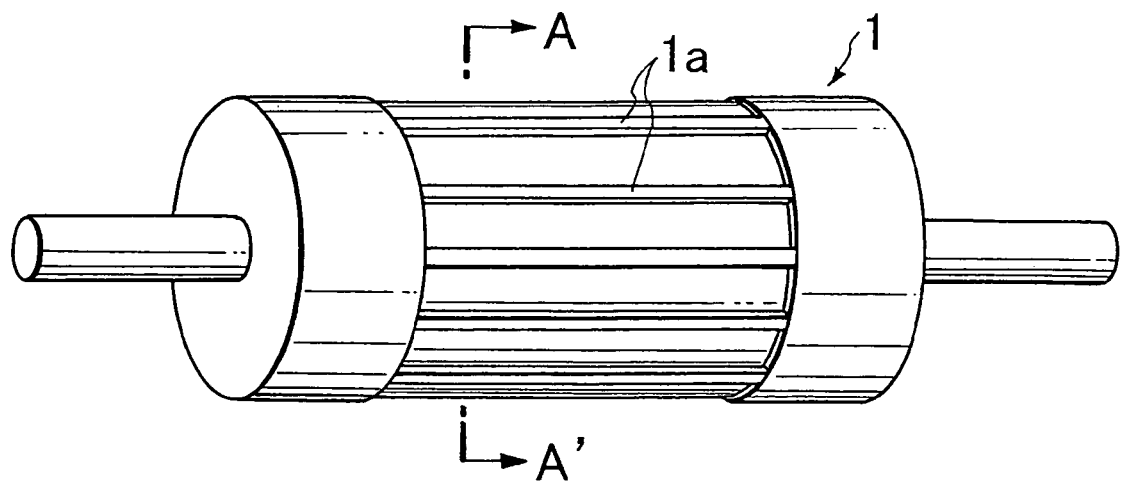
FIG. 4 is a perspective view of the rotating pattern roll used in the pattern coating apparatus as shown in FIG. 3.
Figure 5:
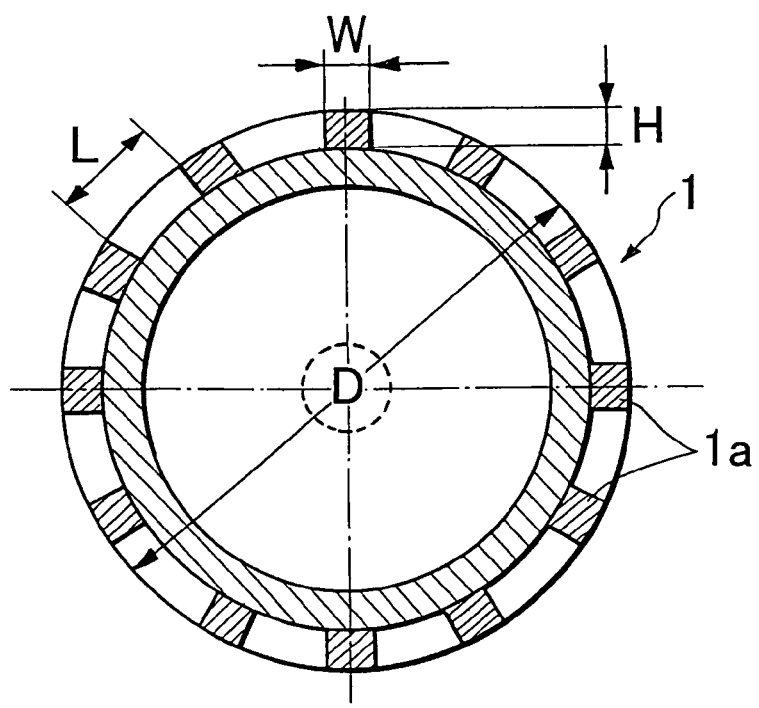
FIG. 5 is a cross-sectional view taken along line A-A' of FIG. 4.

The rotating pattern roll 1 is a roll having a desired convex-and-concave portion on the circumference thereof, an example thereof being shown in FIG. 4. In the example, a plurality of convex portions 1a with a band shape is formed on the circumference surface of the rotating pattern roll 1. For example, as shown in FIG. 5, these convex portions 1a are 12 convex portions with a rectangular cross section, positioned at regular intervals on the circumferential surface of the rotating pattern roll 1, and extending in parallel to the center of the axle of the rotating pattern roll 1. The width, height, and the interval between each of these convex portions 1a determine the shape and size of the coating layer to be formed. There is no limit in particular to these values, but the preferred range is shown as below.

Diameter of the rotating pattern roll (D):
100 to 500 mm
Width of each convex portion (W):
2 to 20 mm
Height of each convex portion (H):
0.1 to 5 mm
Interval between adjacent convex portions (L):
20 to 150 mm In the coating apparatus, the dispersion slurry to be coated on the surface of the substrate sheet 2 is continuously supplied to the surface of the substrate sheet 2 at a discharge position which is positioned just prior to reaching the portion close to the lowest end in the rotating process of the rotating pattern roll 1, through a temporary retaining portion 4 which is installed if necessary.

In addition, a support roll 11, facing opposite the rotating pattern roll 1 with the substrate sheet 2, is installed at the location where the circumferential surface of the rotating pattern roll 1 comes closest to the surface of the substrate sheet 2, the substrate sheet 2 being positioned between the support roll 11 and the rotating pattern roll 1.

Furthermore, a cover film 5 is positioned in such a way that the cover film 5 covers the circumference surface of the rotating pattern roll 1 to prevent the dispersion slurry supplied from the temporary retaining portion 4 from contacting the circumference surface of the rotating pattern roll 1, and that the leading edge of the cover film 5 extends to the space between the rotating pattern roll 1 and the substrate sheet 2. In the coating apparatus, the dispersion slurry is supplied to the space between the leading edge portion of the cover film 5 and the surface of the substrate sheet 2, the space being the location of the discharge position of the dispersion slurry.

The role of a flexible cover film is to convert the convex-and-concave motion of the rotating pattern roll to the extrusion force of the slurry. The cover film, therefore, must have enough flexibility to be able to follow the motion of the rotating pattern roll. The cover film can be divided into three groups, depending on the application to be used in view of the equipment performance, slurry condition, etc. The cover film of the first group has a contraction and expansion elasticity similar to the tube pump. The cover film belonged in the first group includes a stretchable film sheet having 50% or more of rupture elongation, measured by Tensilon, that is, being capable of stretching 1.5 times length of the original cover film, including, for example, polyurethane, butadiene, silicon rubber and nitryl rubber. The cover film belonged in the first group is superior in view of functionality, but not in durability.

The cover film of the second group is a film without contraction and expansion elasticity and having 50% or less of rupture elongation, such as PET film, PP film, cellophane, and Teflon sheet. The thickness of the film is 500 μm or less, preferably 200 to 20 μm. The cover film belong in the second group is superior in view of durability, but not in flexibility.

The cover film of the third group is a member combining the cover film of the first group and the second group. The cover film of the third group is intended to have combined properties of durability and flexibility. The cover film of the first group and the second group is used to form the cover film of the third group such that the cover film of the second group is overlapped with the cover film of the third group wherein the cover film of the second group is in contact with the surface of the roll and the cover film of the first group is in contact with the dispersion slurry. The cover film of the third group is used such that the flexible film of the first group is put together under the film of the second group. The combined use of the cover film of the first group and second group greatly improve the coating stability.

In the example as shown in FIG. 3, the highest end of the cover film 5 is fixed to a fixture 7 at a predetermined position, while the other end of the cover film 5 is a free end between the rotating pattern roll 1 and the substrate sheet 2. It should be noted that the cover film 5 has a length extending from the bottom portion of the rotating pattern roll 1 to a position which is a downstream in view of the traveling direction of the substrate sheet 2.

Preferably, seal plates 12 are provided under the rotating pattern roll 1 closer to the discharge position to prevent a part of the dispersion slurry from leak through the substrate sheet 2 to the lower portion. The seal plates 12 can be provided at the downstream of the support roll 11 if necessary, while, in the figure, the seal plates 12 is only provided at the upstream of the support roll 11.

Figure 6:
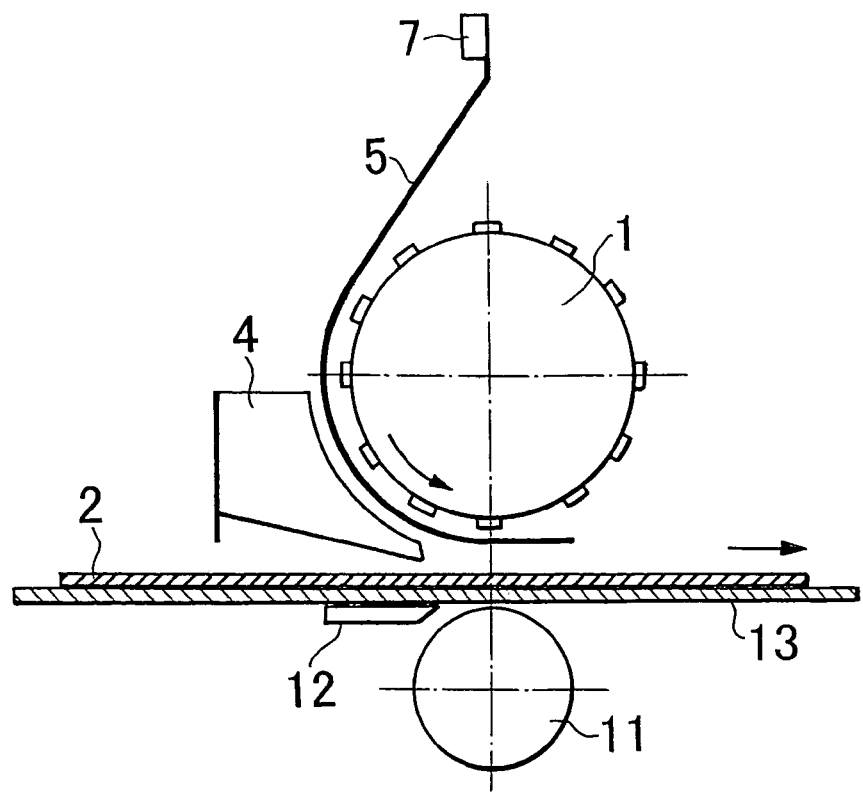
FIG. 6 is a schematic side view of the pattern coating apparatus according to an another aspect of the present invention.

In the coating apparatus according to the present invention, although any of mechanisms for traveling the rotating pattern roll 1 can be used without limitation, an example of the mechanism commonly used is a net conveyer 13, as shown in FIG. 6.

For convenience of drawing and explanation, the rotating pattern roll 1 and the cover film 5 are shown further away from the other elements than they are in real state.

Each constituent element of the coating apparatus for dispersion slurry as shown in FIG. 3 or FIG. 6 will be explained below.

First, the rotating pattern roll 1 is positioned such that a clearance (void space) of prescribed thickness is formed between the lowest end of circumference surface of the rotating pattern roll 1 and the surface of the substrate sheet 2, which continuously travels underneath the rotating pattern roll 1, via the cover film 5. As a consequence, the rotating pattern roll 1 limits the thickness of the dispersion slurry 3 to be coated on the surface of the substrate sheet 2 to a desired value. Further, the distance between the cover film 5 and the surface of the substrate sheet 2 in the direction from the cover film 5 to the substrate sheet 2 is increased and decreased by the plurality of the convex portions 1a provided on the circumference surface of the rotating pattern roll 1. As the result, a first region and a second region of the coating layer are formed on the substrate sheet 2, corresponding to the convex-and-concave pattern of the rotating pattern roll 1 wherein the thickness of the first region is thicker than that of the second region.

Figure 7A:
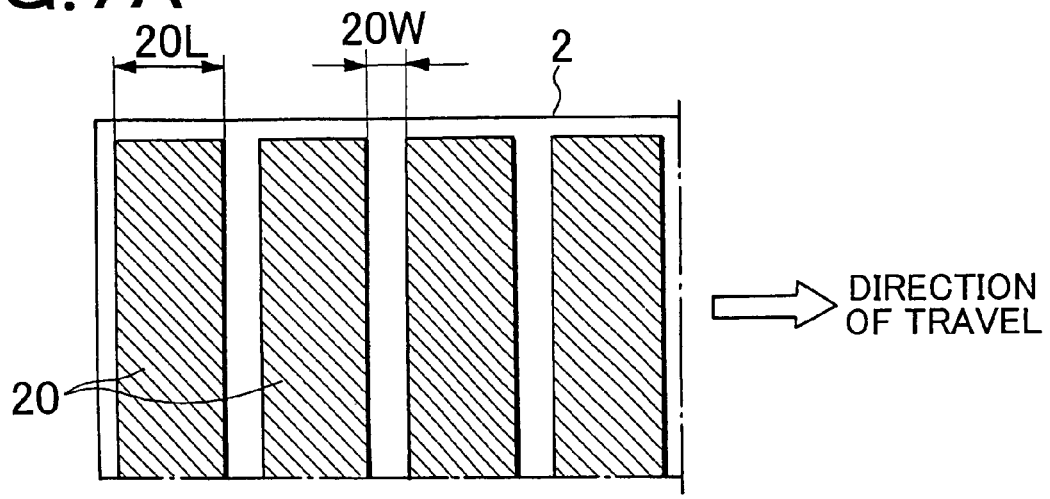
FIGS. 7(A), (B) and (C) are the plan views showing different patterns of the coating layer formed, according to the present invention, on the surface of a substrate.

FIG. 7(A) shows a manufactured sheet obtained by the pattern-coating apparatus shown in FIG. 3 or FIG. 6. A number of bands of coating layer 20 (that is, the first region) in the parallel with each bands is formed on the surface of the substrate sheet 2 wherein each band of the coating layer 20 is separated by the second region which has the thinner coating layer than that of the first region or does not scarcely have the substrate sheet in the band shape. The length of each coating layer 20 (20L) corresponds to the distance (L) between the adjacent convex portions 1a of the rotating pattern roll 1, and the width of the convex portions 1a (20W) corresponds to the width (W) of each convex portions 1a of the rotating pattern roll 1.

Although the distance (L) between the adjacent convex portions 1a of the rotating pattern roll 1 and the length of each coating layer 20 (20L) has the corresponded relationship, the length of each coating layer 20 (20L) is determined by the following three parameters, that is, the distance (L) between the adjacent convex portions 1a of the rotating pattern roll 1, the traveling speed of the substrate sheet 2 and the rotating speed of the rotating pattern roll 1. The distance (L) between the adjacent convex portions 1a of the rotating pattern roll 1 and the length of each coating layer 20 (20L) is substantially equal if the traveling speed of the substrate sheet 2 is same as the rotating speed of the rotating pattern roll 1, that is, (the speed of the substrate sheet 2)/(the rotating speed of the rotating pattern roll 1)=1.0. When the traveling speed of the substrate sheet 2 is relatively higher than the rotating speed of the rotating pattern roll 1, the length of each coating layer 20 (20L) is shorter than the above-mentioned length. On the other hand, when the traveling speed of the substrate sheet 2 is relatively lower than the rotating speed of the rotating pattern roll 1, the length of each coating layer 20 (20L) is longer than the above-mentioned length. For example, in the case of (the speed of the substrate sheet 2)/(the rotating speed of the rotating pattern roll 1)=1.5, the length of each coating layer 20 (20L) is 1.5 times of the distance (L) between the adjacent convex portions 1a of the rotating pattern roll 1. On the other hand, in the case of (the speed of the substrate sheet 2)/(the rotating speed of the rotating pattern roll 1)=0.5, the length of each coating layer 20 (20L) is approximately 2.0 times of the distance (L) between the adjacent convex portions 1a of the rotating pattern roll 1.

In the example mentioned, the coating layer having same range with respect of the full length of the substrate sheet 2 is formed. If it is desired that the coating layer thus formed as above-mentioned is divided into a plurality of region along the width direction of the substrate sheet 2, the dispersion slurry is supplied in the plural bands formed of a desired width. The pattern-coating apparatus structured to form such coating layer is shown in FIG. 8.

Figure 8:
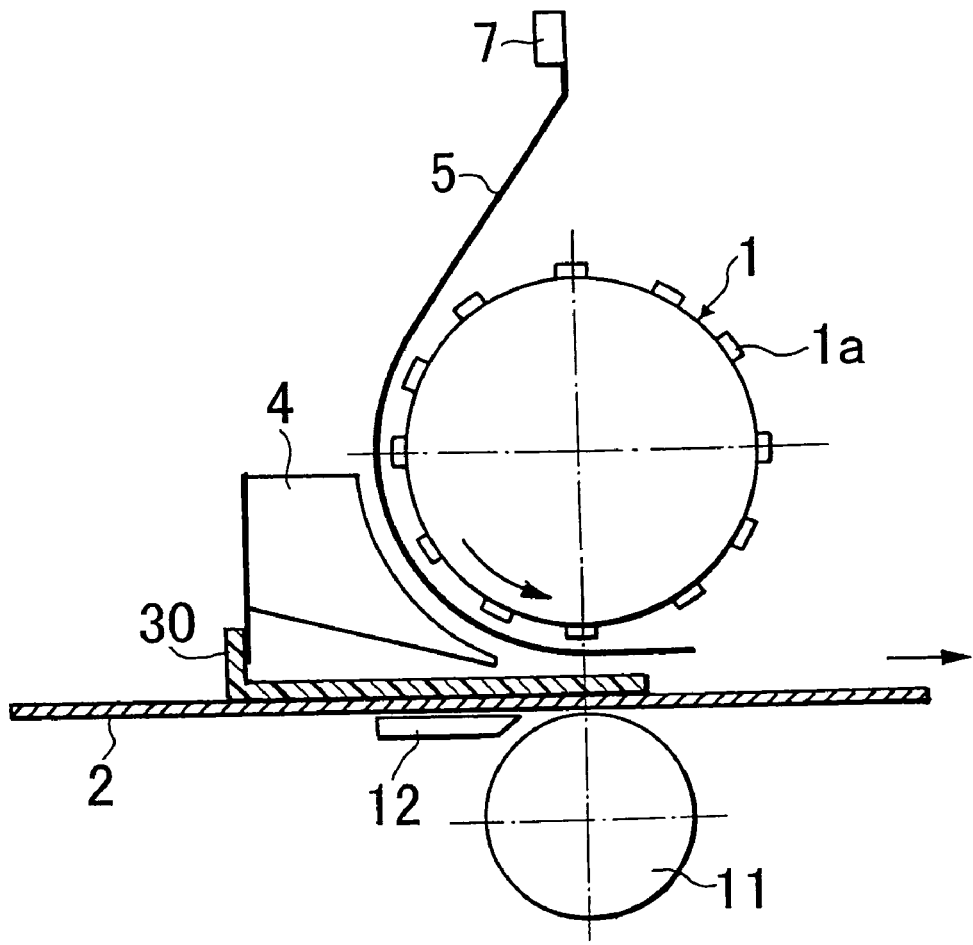
FIG. 8 is a schematic side view of the pattern coating apparatus according to a further another aspect of the present invention.
Figure 9:
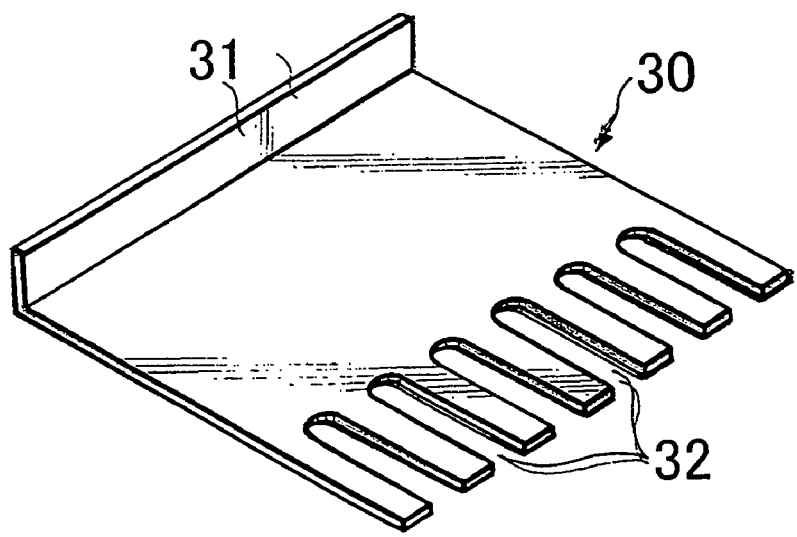
FIG. 9 is a perspective view showing the line coating plate used in the pattern coating apparatus as shown in FIG. 8.

Because there are many common elements between the pattern-coating apparatus shown in FIG. 8 and the one shown in FIG. 6, the same reference numerals is put into the identical or equivalent portions, and the detailed explanations thereof are omitted. The difference between the pattern-coating apparatuses as shown in FIGS. 8 and 6 is only that a line-coating plate 30 is installed, which is positioned above the surface of the substrate sheet 2 so as to extend from the dispersion slurry feed opening at the temporary retaining portion 4 through underneath the rotating pattern roll 1 and to reach near the leading edge of the cover film 5. The line-coating plate 30, as shown in FIG. 9, is a substantially-flattened L-shape plate comprising a locking part 31 upwardly extended at its front end, that is, at its upstream end in the traveling direction of the substrate sheet 2. A plurality of apertures 32, each of which is parallel and extends in the upstream end in the traveling direction of the substrate sheet 2, is formed at the downstream end in the traveling direction of the substrate sheet 2. The apertures 32 is fixed at a position where the circumference surface of the rotating pattern roll 1 is closest to the substrate sheet 2.

Figure 10A:
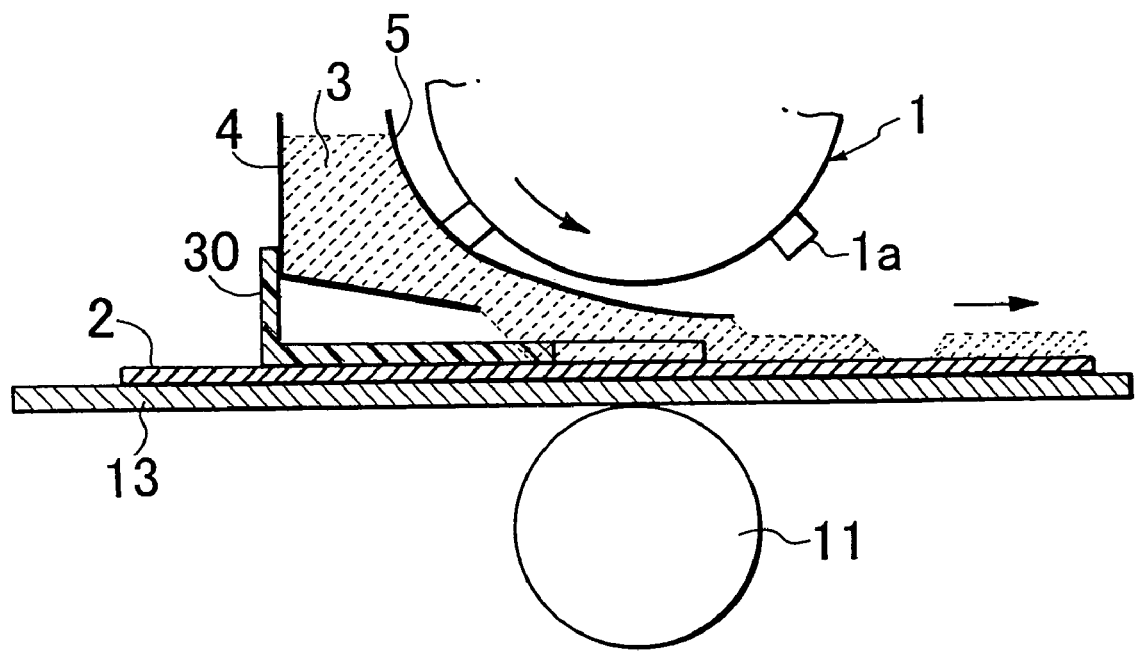
FIGS. 10(A) and (B) are explanatory drawings showing the process of forming the pattern on the coating layer in the pattern coating apparatus as shown in FIG. 8.
Figure 10B:
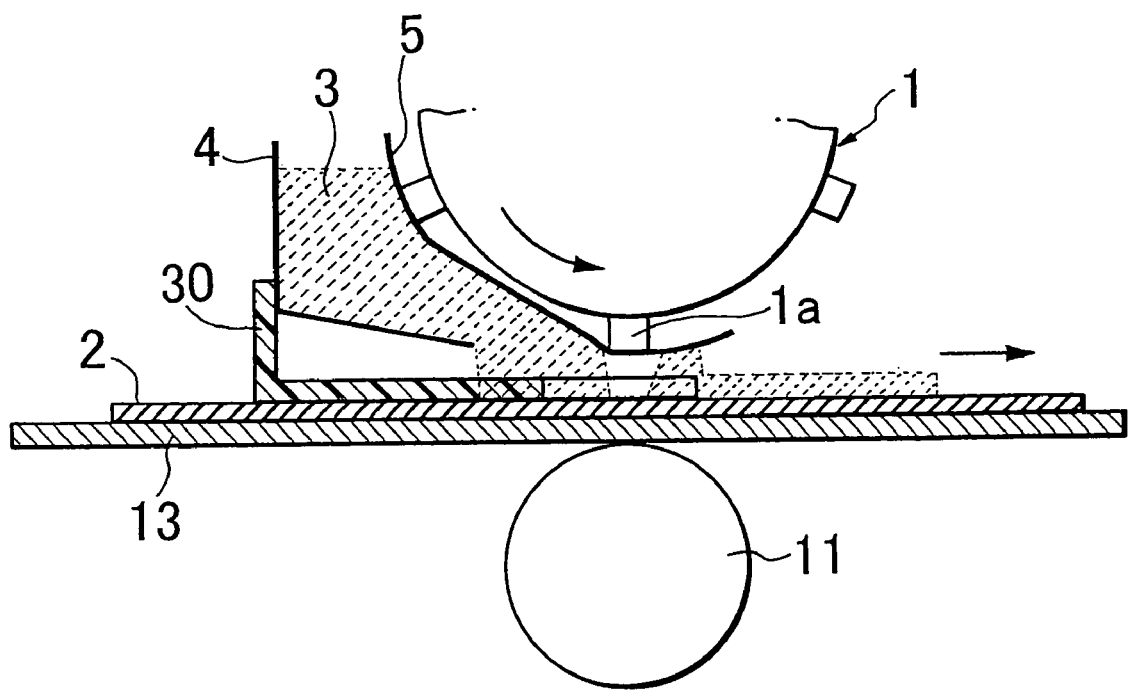

FIGS. 10(A) and 10(B) schematically show the process for forming the coating layer 20 on the surface of the substrate sheet 2 by the pattern-coating apparatus as shown in FIG. 8. In these figures, for convenience of drawing and explanation, the rotating pattern roll 1 and the cover film 5 are shown further away from the other elements than they are in real state.

FIG. 10(A) shows a state where the concave portion formed between the convex portions 1a of the rotating pattern roll 1 is closer to the front end of the line-coating plate 30. In the state, the dispersion slurry 3 is supplied on the line-coating plate 30 from the outlet of the temporary retaining portion 4, wherein the supplied dispersion slurry is in the sheet state, and the width thereof is narrower than the full length of the substrate sheet 2. Then, the supplied dispersion slurry is divided into the same number of band as that of the apertures 32 via the apertures 32 of the line-coating plate 30. As the result, the coating layer 20 is formed on the substrate sheet 2.

Then, when the convex portions 1a is reached on the apertures 32 of the line-coating plate 30 by the rotation of the rotating pattern roll 1, the cover film 5 being in contact with the convex portions 1a is downwardly pressed in the perpendicular direction of the substrate sheet 2, thereby suppressing the supply of the dispersion slurry 3 or greatly decreasing the amount of the supply of dispersion slurry 3. Since the substrate sheet 2 is, however, moved during the above-mentioned process, the coating layer 20 will not be formed or be thinner formed, until the convex portions 1a of the rotating pattern roll 1 is passed from the position.

After the convex portions 1a of the rotating pattern roll 1 is passed from the upper portion of the apertures 32 of the line-coating plate 30 by the rotation of the rotating pattern roll 1, the supply of the dispersion slurry 3 is recovered as shown in FIG. 10(A).

Figure 7B:
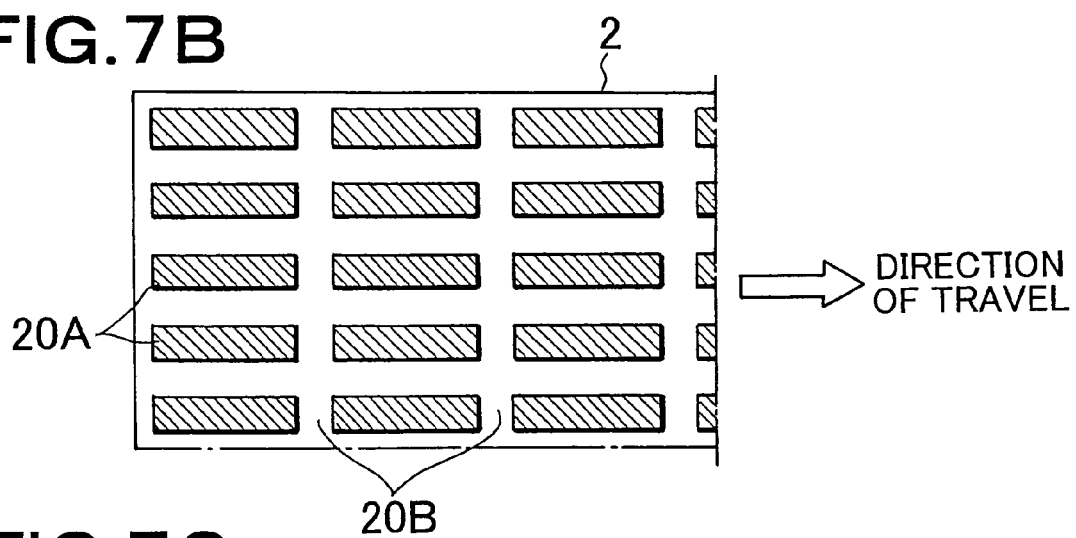

A pattern of the coating layer 20 is formed on the surface of the substrate sheet 2 by the above-mentioned processes, as shown in FIG. 7(B). The pattern has a repeated pattern of a first region 20A and a second region 20B wherein the first region 20A is in a parallel band shape each other with respect to the width direction of the substrate sheet 2, and the second region 20B has the thin coating layer 20 or does not scarcely have the coating layer 20.

In the pattern as shown in FIG. 7(B), the first region 20A having a thick coating layer 20 is shown as the rectangular shape. However, the shapes of the first region 20A during the real coating process are nearly infinite forms, since the second region 20B is formed by indirectly pushing the dispersion slurry 3 with the convex portions 1a of the rotating pattern roll 1 via cover film 5.

Figure 11A:
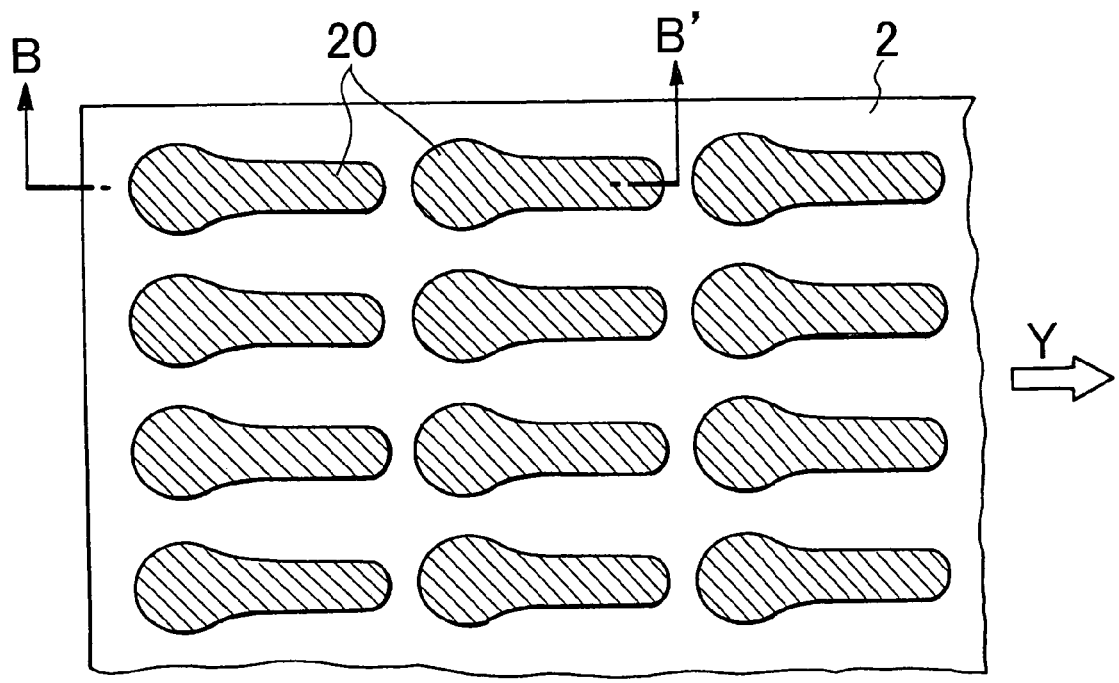
FIG. 11 is a view showing the pattern of the coating layer as shown in FIG. 7(B) in the closer shape to the real pattern according to the process of the present invention wherein (A) is a plan view and (B) is a an enlarged sectional view.
Figure 11B:
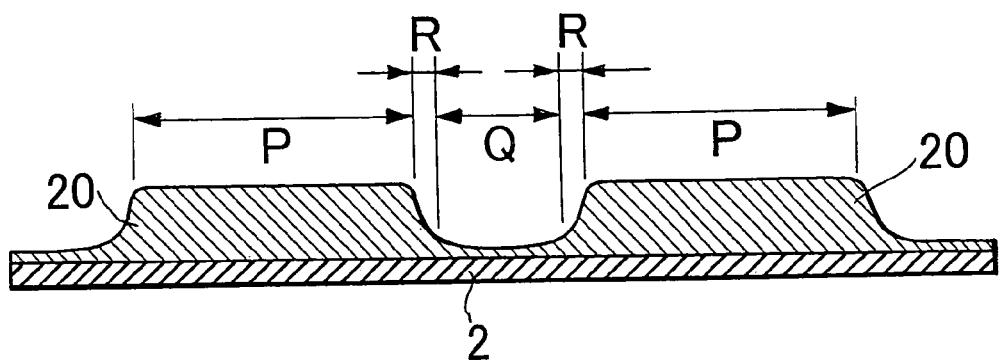

The FIG. 11(A) shows a plan view of the closer shape to the real pattern, according to the process of the present invention, corresponding to the coating pattern as shown in FIG. 7(B), and the FIG. 11(B) the enlarged sectional view along the B-B' line as shown in FIG. 11(A). The first region (P) having the thick coating layer, surrounded by the second region (Q) is formed on the surface of the substrate sheet 2 wherein the second region (Q) has a thin coating layer or does not scarcely have the coating layer. The dispersion slurry remained in the portion is put into the forward in view of the traveling direction of the substrate sheet 2, since the convex portions of the rotating pattern roll 1 downwardly push the dispersion slurry via the cover film in the coating apparatus according to the present invention. As the result, each of coating layers 20 tend to be formed such that, with respect to the longitudinal direction of the substrate sheet 2 (i.e. the traveling direction of the substrate sheet 2 during coating procedure, as indicated arrow Y), the width of the front end thereof is narrower than that of the rear end thereof. A transition region (R) is formed at both end of the coating layer 20 in the longitudinal direction of the substrate sheet 2 wherein the thickness of the transition region (R) is decreased as the transition region (R) is closer to the second region formed between the adjacent coating layers 20.

Figure 12:
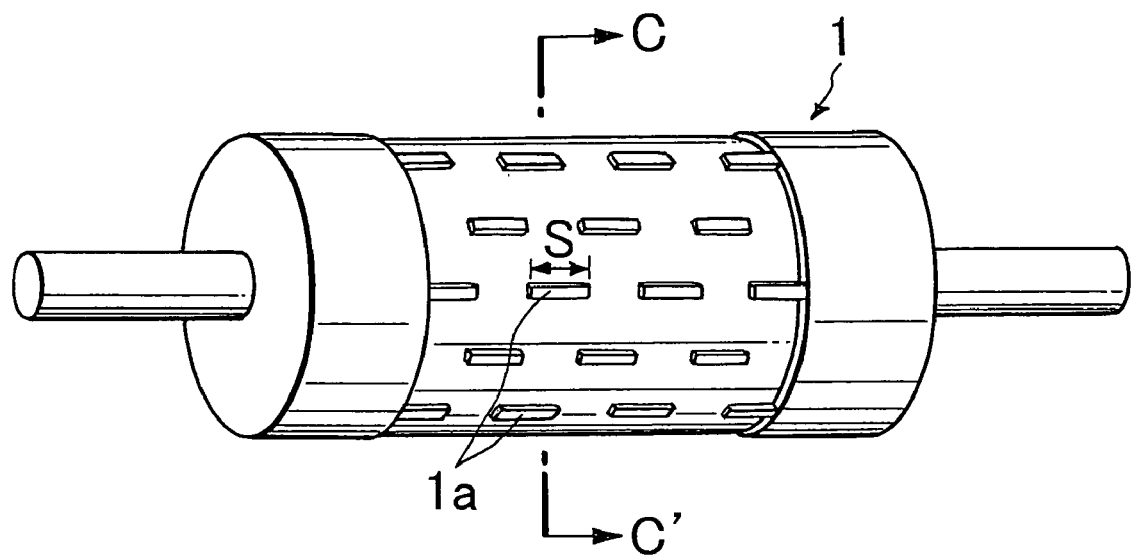
FIG. 12 is a perspective view showing an another example of the rotating pattern roll applied in the pattern coating apparatus of the present invention.
Figure 13:
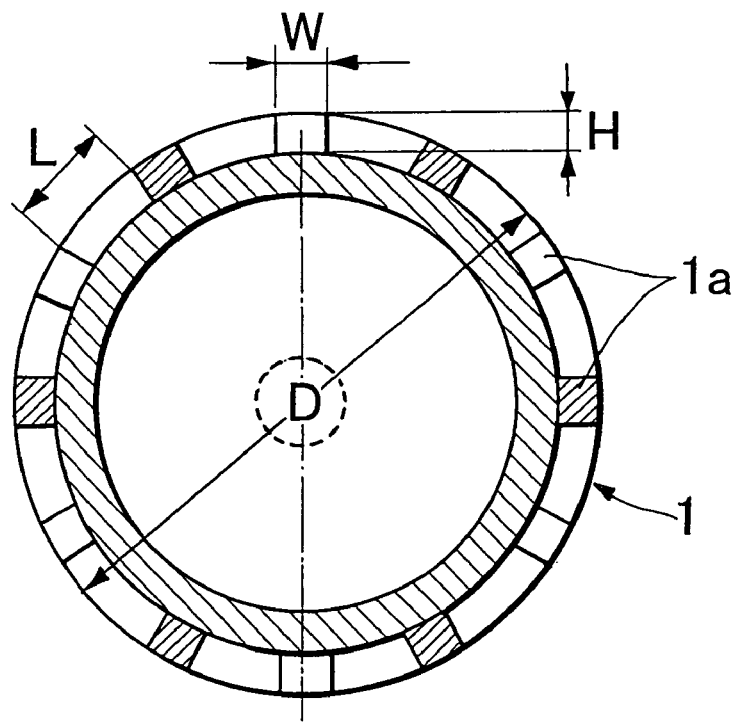
FIG. 13 is a cross-sectional view taken along line C-C' as shown in FIG. 12.

FIG. 12 shows another example of the rotating pattern roll 1 applied to the present invention. FIG. 13 is an enlarged cross-sectional view along the line C-C'. The rotating pattern roll 1 of the example, comprises a plurality group of convex portions 1a provided in the offset position in the circumferencial direction of the circumference surface. Each group of the convex portions 1a is positioned to be in offset with the adjacent group of the convex portions 1a by appropriate alignment along the axial direction of the rotating pattern roll 1.

Figure 7C:
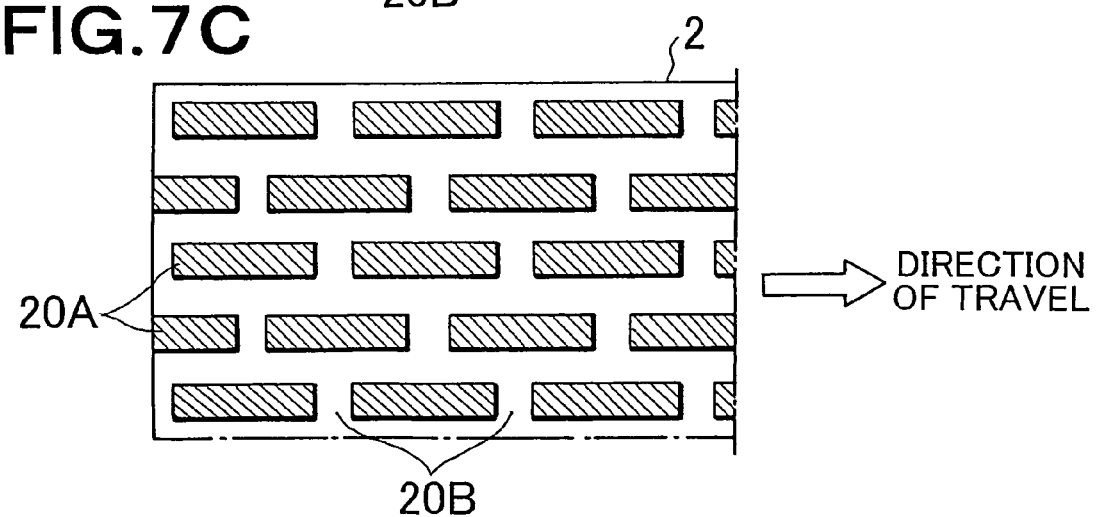

In case of using the rotating pattern roll 1 having the convex portions 1a as provided in the above-mentioned pattern, the coating layer 20 indicating the pattern as shown in FIG. 7(C) will be formed.

It should be noted that any patterns provided as the convex portions 1a can be selected in accordance with any applications without being limited in the pattern as shown in FIGS. 4 and 12.

Figure 14:
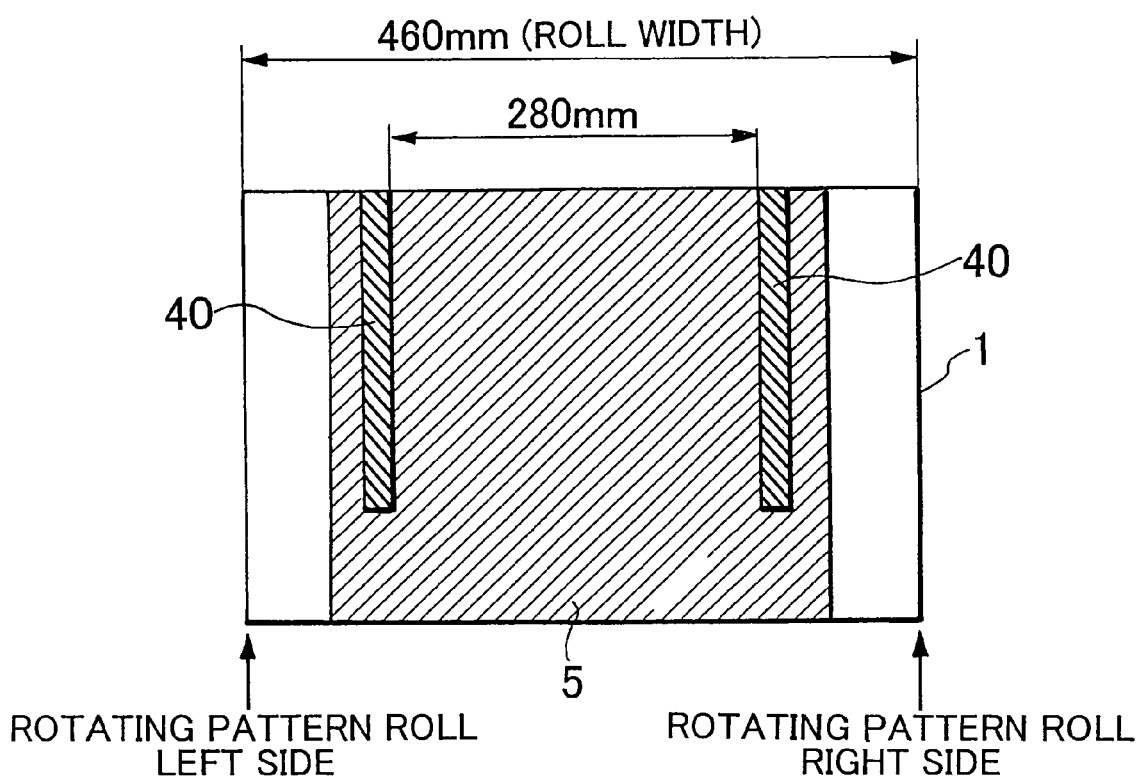
FIG. 14 is an explanatory view showing the planar positional relationship between the side seal, the rotating pattern roll and the cover film, applied in the pattern coating apparatus of the present invention.

In the pattern-coating apparatus according to the present invention, as same as to the conventional roller coating apparatus, it may be desired that the coated range is limited in the width direction of the moving substrate. FIG. 14 shows an example of a member for limiting the range of the coating in the width direction. In the figure, there is shown the rotating pattern roll 1, the cover film 5 and a side seals 40 and there is not shown other element thereof.

The side seals 40 comprises a pair of plates positioned at both end thereof, each of which is designed to be as a gate for both side of the temporary retaining portion 4. In order to prevent liquid leakage by closely contacting the surface of the rotating pattern roll 1 and the rear plate portion, they are positioned outside the side portions on both sides of the cover film 5, and are fixed on the side walls of the temporary retaining portion 4 with bolts and nuts, etc.

It is preferable that these side seals 40 are installed to contact the circumferential surface of the rotating pattern roll 1, to prevent the dispersion slurry from leaking, through the void space between the circumferential surface of the rotating pattern roll 1 and the side seals, to outside the side seals. In this case, however, the side seals with sealing capability against the circumferential surface of the rotating pattern roll 1, and as well as with low friction resistance, and moreover with little frictional wear, are suitable. In order to satisfy these requirements, it is preferred that these side seals 40 consist of the resin material selected from synthetic rubber, expanded foam or Teflon®, etc.

To ensure sufficient flexibility when bending in the absorbent sheet obtained by applying the present invention, a relationship between a length of the first region having the thick coating layer 20, hereinafter referred to as P, a length of the second region, hereinafter referred to as Q, and a length of the transition region formed between the first region and the second region, hereinafter referred to as R, will be desirably in a range as follows:

P>Q

Q: 2 to 300 mm

It is preferable that Q: 5 to 30 mm.

Further, the amount of SAP contained in the first region and the second region is preferred to be in a range as follows:

P: 100 to 500 g/m$^2$

Q: 10 to 150 g/m$^2$

A superior absorbing properties of the highly-water-absorbing sheet comprising the coating layer 20 with appropriate size and thickness provided on the surface of the substrate sheet 2 will be obtained as a high water-absorbing sheet, in comparison with a sheet comprising the coating layer with constant thickness provided on all of the surface of a substrate. That is, when a liquid is supplied on the surface of the highly-water-absorbing sheet manufactured by the method according to the present invention, a part of the liquid is absorbed by the water-absorbing properties of the SAP contained in the coating layer 20. In this case, the other part of the liquid is in contact with the second region positioned around them, since the liquid will not be immediately absorbed, due to not-highly-absorbing speed of the SAP. Then, the other part of the liquid is immediately dispersed by the storage capacity and the dispersing capacity of the second region, thereby extremely minimizing the time for remaining the liquid intact. Therefore, the leakage of the liquid will be effectively prevented.

Further, in the absorbing body in sheet having the coating layer 20, by using the coating pattern as shown in FIG. 7(A), the flexibility in the longitudinal direction is excellent, the body is easily cut during the cutting process, and the amount of the dust caused during the cutting process can be suppressed.

In the case of using the coating patter as shown in FIG. 7(B), since the second region which have a thin coating layer or does not scarcely have it is formed in both of the longitudinal and width direction, the flexibility can be obtained in both of the longitudinal and width directions, the amount of the dust caused by folding and/or cutting can be suppressed.

INDUSTRIAL APPLICABILITY

As explained above, according to the present invention, because the first region, where a thick coating layer is present, and the second region, where a thin coating layer is present, or the coating layer is scarcely present, are formed on the surface of the substrate sheet, excellence in absorption effect and flexibility in the longitudinal direction and/or the width direction of the substrate sheet is achieved, making it possible to minimize generation of dust when bending or cutting.

In addition, by appropriately selecting the convex-and-concave pattern formed on the circumferential surface of the rotating pattern roll, flexibility when bending the obtained absorbent sheet is made adjustable, making it possible to easily obtain-performance suited to the purpose, as well as handling, when this is applied to the absorbent products.

The present invention's method and apparatus, with these characteristics, have a great deal of potential in industry.

The present invention's method and apparatus, with these characteristics, have a great deal of potential in industry.

What is claimed is:

1. An apparatus for pattern-coating a dispersion slurry containing a water-absorbing solid dispersed in a dispersion medium on a substrate sheet, comprising:
   a traveling mechanism for traveling said substrate sheet into the longitudinal direction thereof
   a rotating pattern roll having a predetermined convex-and-concave pattern on the circumference surface thereof such that the center of axle is vertically positioned;
   a cover film for covering the circumference surface of said rotating pattern roll to prevent said dispersion slurry from being contact with the circumference surface of said rotating pattern roll, a front end of said cover film being positioned in the downstream from the lowest position of said rotating pattern roll; and
   a slurry supplier for continuously supplying said dispersion slurry on the said substrate sheet from a discharge portion of said supply supplier at a outlet position being positioned between said cover film and said substrate sheet;
   wherein the surface of the substrate sheet having formed thereon a first region and a second region, the thickness of the first region of the coating layer is thicker than the second region, the thickness of the coating layer in the second region is thinner or does not have the coating layer, and wherein the pattern corresponds to the pattern of the convex-and-concave portion of the rotating pattern roll by pushing the coating film via the rotating pattern roll into the surface of the coating layer.

2. The apparatus for coating as claimed in claim 1, wherein said front end of said cover film is not fixed to any members.

3. The apparatus for coating as claimed in claim 2,
wherein the diameter of said rotating pattern roll is 100 to 500 mm, and
said front end of said cover film is extended by 1 to 50 mm to the downstream from the lowest position of said rotating pattern roll in the traveling direction of said substrate sheet.

4. The apparatus for coating as claimed in claim 1, wherein said cover film except said front end thereof is fixed at both ends in the axis direction of said rotating pattern roll by a side seal.

5. The apparatus for coating as claimed in claim 4, wherein a length, in the rotating direction of said rotating pattern roll, of each convex portion of said convex-and-concave pattern formed in the circumference surface of said rotating pattern roll is smaller than the length between the rear end of one of said convex portion and a front end of the adjacent one of said convex portion.

6. The apparatus for coating as claimed in claim 5, wherein the length of the convex portion of said rotating pattern roll is 20 to 150 mm.

7. The apparatus for coating as claimed in claim 1, wherein said slurry supplier includes a line-coating plate for supplying said dispersion slurry with band shape on the surface of said substrate sheet.

8. The apparatus for coating as claimed in claim 1, further comprising a support roll facing opposite said rotating pattern roll such that said substrate sheet travels there between at the closest position of the surface of said substrate sheet to the circumference surface of said rotating pattern roll.

9. The apparatus for coating as claimed in claim 1, wherein a seal plate for preventing said dispersion slurry from falling down and passing through said substrate sheet is provided at a position where said dispersion slurry is supplied on the surface of said substrate sheet.

10. The apparatus for coating as claimed in claim 1, wherein said traveling mechanism is a conveyer for traveling said substrate sheet.

11. The apparatus for coating as claimed in claim 1,
wherein said slurry supplier is a temporary retaining portion for said dispersion slurry, and
wherein said substrate sheet is positioned just on said traveling mechanism;
said cover film is positioned on said substrate sheet;
said rotating pattern roll is positioned above said cover film;
said discharge portion of said supply supplier of said temporary retaining portion is the lowest portion of said rotating pattern roll in the upstream direction.

* * * * *